(12) United States Patent
Weng (10) Patent No.: US 8,890,526 B2
(45) Date of Patent: Nov. 18, 2014

(54) METHOD AND APPARATUS FOR MAKING DISTINCTION IN A MAGNETIC RESONANCE IMAGING WATER-FAT IMAGE

(75) Inventor: De He Weng, Shenzhen (CN)

(73) Assignee: Siemens Aktiengesellschaft, Munich (DE)

( * ) Notice: Subject to any disclaimer, the term of this patent is extended or adjusted under 35 U.S.C. 154(b) by 448 days.

(21) Appl. No.: 13/339,660

(22) Filed: Dec. 29, 2011

(65) Prior Publication Data

US 2012/0169337 A1    Jul. 5, 2012

(30) Foreign Application Priority Data

Dec. 29, 2010   (CN) .......................... 2010 1 0610002

(51) Int. Cl.
| | | |
|---|---|---|
| *G01R 33/48* | (2006.01) | |
| *G01R 33/34* | (2006.01) | |
| *A61B 5/00* | (2006.01) | |
| *A61B 5/055* | (2006.01) | |

(52) U.S. Cl.
CPC ............... *A61B 5/055* (2013.01); *A61B 5/4872* (2013.01); *A61B 5/4875* (2013.01)
USPC ........................... 324/309; 324/307; 324/318

(58) Field of Classification Search
CPC .... A61B 5/4872; A61B 5/4875; A61B 5/055; G01R 33/4828; G01R 33/485; G01R 33/5607
USPC .................................................. 324/300–322
See application file for complete search history.

(56) References Cited

U.S. PATENT DOCUMENTS

| | | | |
|---|---|---|---|
| 5,909,119 A * | 6/1999 | Zhang et al. .................. | 324/309 |
| 2006/0241381 A1 | 10/2006 | Wang et al. | |
| 2010/0239149 A1 | 9/2010 | Wang et al. | |

\* cited by examiner

*Primary Examiner* — Melissa Koval
*Assistant Examiner* — Rishi Patel
(74) *Attorney, Agent, or Firm* — Schiff Hardin LLP (57) ABSTRACT

In a method and an apparatus for making a distinction in a magnetic resonance imaging water-fat image, three echoes are acquired without phase encoding as a reference scan, a reference water-fat image projection is calculated in the phase encoding direction using the reference scan, a complete water-fat image projection is calculated in the phase encoding direction according to a water image and a fat image obtained by a three-point Dixon method, a correlation between the reference water-fat image projection and the complete water-fat image projection is calculated to obtain at least two correlated values, and the maximum correlated value is acquired therefrom, so as to determine the type of said image calculated by using the three-point Dixon method.

12 Claims, 5 Drawing Sheets

METHOD AND APPARATUS FOR MAKING DISTINCTION IN A MAGNETIC RESONANCE IMAGING WATER-FAT IMAGE

BACKGROUND OF THE INVENTION

1. Field of the Invention

The present invention relates to magnetic resonance imaging and in particular to a method and an apparatus for making a distinction in a magnetic resonance imaging water-fat image.

2. Description of the Prior Art and Related Subject Matter

Magnetic resonance imaging is an imaging modality using the magnetic resonance phenomena. The principles of the magnetic resonance phenomena are fundamentally as follows. The protons of nuclei that contain singular protons (such as hydrogen nuclei that are widely existing in human bodies) have self-spin motion and behave like small magnets, and the self-spin axes of these small magnets have no certain rules; if an external magnetic field is applied thereto, these small magnets rearrange according to the external magnetic field's magnetic force lines, meaning they arrange in two directions which are parallel to or oppositely parallel to the external magnetic field's magnetic force line. The direction that is parallel to the external magnetic field's magnetic force line is referred to as a positive longitudinal axis, and the direction that is oppositely parallel to the external magnetic field's magnetic force line is referred to as a negative longitudinal axis. The nuclei have only a longitudinal magnetization component, and this longitudinal magnetization component not only has a direction but also an amplitude. Radio frequency (RF) pulses at a specific frequency are used to excite the nuclei in the external magnetic field, such that the self-spin axes of these nuclei deviate from the positive longitudinal axis or the negative longitudinal axis and resonate, which is the magnetic resonance phenomenon. After the self-spin axes of the above excited nuclei have deviated from the positive longitudinal axis or the negative longitudinal axis, the nuclei have horizontal magnetization components.

After the radio frequency pulse transmission has stopped, the excited nuclei emit echo signals, due to gradually releasing the absorbed energy, in the form of electromagnetic waves, with both the phase and energy level thereof restoring to the state before being excited. An image can be reconstructed by further processing (such as the spatial encoding, etc.) the echo signals emitted by the nuclei. The process of the excited nuclei returning to the state before being excited is referred to as the relaxation process, and the time required for restoring to the equilibrium state is referred to as the relaxation time.

Inside a human body, the molecular environments in which the hydrogen nuclei in fat and the hydrogen nuclei in water exist are different, so when the excitation is carried out using the same radio frequency pulses, their resonant frequencies are different and the relaxation times are also different. When signals are acquired at different echo times, the fat tissue and the water show different phases and signal strengths.

The Dixon method is a method for producing a pure water proton image in magnetic resonance imaging, and its basic principles are as follows. Two kinds of echo signals, in phase and out phase, of the water and fat protons are respectively acquired and a pure water proton image is produced by calculating these two kinds of signals with different phases and removing the fat signal therein, thus achieving the object of fat suppression. The drawbacks of the Dixon method are that the influence of the magnetic field inhomogeneity thereon is relatively large, it is easily affected by respiratory movements, and the calculation method thereof is complicated and prone to errors.

In order to simultaneously obtain the separated pure water and pure fat images, an improved three-point Dixon method is widely used, and the principles of this method are as follows. One in-phase (or out-of-phase) image and two out-of-phase (or in-phase) images are obtained simultaneously, the added phase caused by the magnetic field inhomogeneity is produced according to these two out-of-phase (or in-phase) images, a phase correction is carried out on these two out-of-phase (or in-phase) images, and then it is used together with the in-phase (or out-of-phase) image to produce a water and fat image.

There are various particular operation processes of the three-point Dixon method, for example, with the use of one in-phase image and two out-of-phase images are used, a method for reconstructing a water-fat separation image is disclosed in Chinese patent application 200510008973.0, that includes the steps of acquiring one in-phase image and two out-of-phase images, obtaining the distribution of the data coil sensitivity of each channel, synthesizing an image of each channel, solving the phase difference of the two out-of-phase images, detecting some feature areas in the in-phase image to be used as criteria for the phase correction, and correcting the phases of the out-of-phase images and calculating images of water and fat.

In addition, a method for implementing water and fat separation is disclosed in Chinese patent application 200910119608.5, that includes the steps of acquiring an in-phase image and two out-of-phase images, calculating the phase difference of said two out-of-phase images, and correcting the phase caused by the magnetic field inhomogeneity in the two out-of-phase images using this phase difference, correcting the linear phase difference caused by the eddy current in the in-phase image by using the two corrected out-of-phase images, and obtaining, by the calculation, a water image and a fat image according to the three corrected images.

Figure 1:
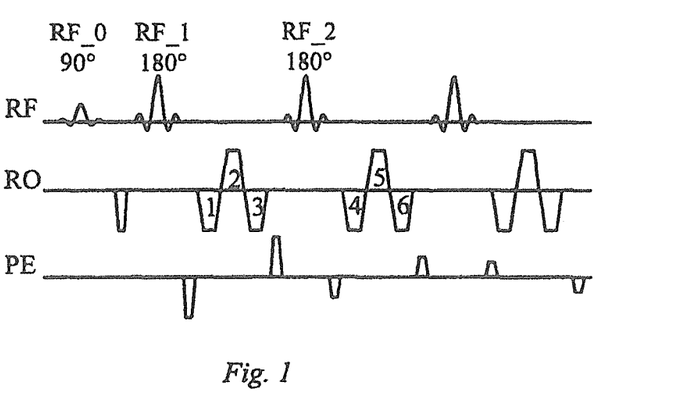
FIG. 1 is a schematic diagram of acquiring the data acquisition and encoding sequences of two out-of-phase images and one in-phase image with a three-point Dixon method which is based on a turbo spin echo sequence in the prior art.

FIG. 1 shows a schematic diagram for acquiring data and encoding sequences of two out-of-phase images and one in-phase image with a three-point Dixon method which is based on a turbo spin echo (TSE) sequence. In this case, RF, RO and PE correspond to a radio frequency pulse, a read out gradient and an encoding gradient, respectively.

As shown in FIG. 1, magnetic resonance imaging equipment first transmits a 90 degree radio frequency pulse RF_0, and then transmits again a 180 degree reunion phase radio frequency pulse RF_1. After an echo time (TE) from the 90 degree radio frequency pulse RF_0, the magnetic resonance imaging equipment applies a read out gradient in the read out gradient direction and reads out three echoes 1, 2, and 3, respectively. Subsequently, a 180 degree reunion phase radio frequency pulse RF_2 is transmitted again and the read out gradient is applied in the read out gradient direction, with three echoes 4, 5 and 6 being read out respectively; and the above operation can be repeated many more times. The sequences in FIG. 1 are continuously repeated after the phase encoding gradient has been changed until all the echoes in the k space are read out. In this case, the data lines corresponding to echoes 1, 4, 7, . . . and so on constitute original data of an out-of-phase image, and the data lines corresponding to echoes 2, 5, 8, . . . and so on constitute original data of an in-phase image, and the data lines corresponding to echoes 3, 6, 9, . . . and so on constitute original data of another out-of-phase image. Data in different rows in the k space are obtained by appropriately modulating these echoes using the phase encoding gradient applied in the phase encoding direction, and when the k space is filled up, the corresponding one in-phase image and two out-of-phase images are constituted after having carried out Fourier transform.

However, the defects in the currently available three-point Dixon method are as follows: since the added phase solved using the two, out-of-phase (in-phase) images cannot be directly used to correct their phases, the anti-wrapping has to be carried out on the phases, and due to the inherent instability of phase anti-wrapping, sometimes the calculated images of water and fat may be shifted, i.e. it is actually the image of water, but the image which has been worked out appears to be the image of fat, or it is actually the image of fat, but the image which has been worked out appears to be the image of water.

Aiming at such a water-fat image shift problem, currently there is not yet a solution corresponding thereto, and to this, how to determine whether a current water (fat) image calculated in the magnetic resonance imaging equipment is actually the image of water or that of fat has already become an urgent problem to be solved in magnetic resonance imaging technology.

SUMMARY OF THE INVENTION

An object of the present invention is to provide a method and an apparatus for making a distinction in a magnetic resonance imaging water-fat image, so as to determine the precise type of a calculated water/fat image.

The method for making a distinction in a magnetic resonance imaging water-fat image provided by the present invention includes:

acquiring three echoes without phase encoding as a reference scan;

calculating a reference water image projection and/or a reference fat image projection in the phase encoding direction using the reference scan, so as to obtain a reference water-fat image projection;

calculating a complete water image projection and/or a complete fat image projection in the phase encoding direction according to a water image and a fat image obtained by calculation using a three-point Dixon method, so as to obtain complete water-fat image projection;

calculating the correlation between the reference water-fat image projection and the complete water-fat image projection, so as to obtain at least two correlated values; and acquiring the maximum correlated value from the correlated values obtained by calculation, and determining the type of said complete image projection corresponding to said maximum correlated value as the type of a reference image projection corresponding to the maximum correlated value, so as to determine the type of the image obtained by calculation using the three-point Dixon method according to the type of the complete image projection.

The apparatus for making a distinction in a magnetic resonance imaging water-fat image provided by the present invention includes:

a reference scan acquisition unit for acquiring three echoes without phase encoding as a reference scan;

a reference image projection calculation unit for calculating a reference water image projection and/or a reference fat image projection in the phase encoding direction using the reference scan, so as to obtain a reference water-fat image projection;

a complete image projection calculation unit for calculating a complete water image projection and/or a complete fat image projection in the phase encoding direction according to a water image and a fat image obtained by calculation using a three-point Dixon method, so as to obtain a complete water-fat image projection;

a correlation calculation unit for calculating the correlation between the reference water-fat image projection and the complete water-fat image projection, so as to obtain at least two correlated values; and a result judgment unit for acquiring the maximum correlated value from the correlated values calculated by said correlation calculation unit, determining the type of the complete image projection corresponding to the maximum correlated value as the type of a reference image projection corresponding to the maximum correlated value, so as to determine the type of a corresponding image calculated by using the three-point Dixon method according to the type of the complete image projection.

It can be seen from the solutions described above that in the embodiments of the present invention, three echoes without phase encoding are used as a reference scan and a reference water image projection and a reference fat image projection in the phase encoding direction are calculated using this reference scan to obtain an image projection, the water-fat type of which is precise; then the reference water image projection and the reference fat image projection are used as standards, correlation calculation is carried out on the complete water image projection and the complete fat image projection in the phase encoding direction obtained by calculation of the water image and the fat image obtained according to the three-point Dixon method, and in the water-fat image obtained by the three-point Dixon method is made a distinction according to the correlation value, thus solving the water-fat image shift problem in the prior art.

Furthermore, by carrying out the normalization processing on the reference water image projection and the reference fat image projection before carrying out the correlation calculation, the reference water image projection and the reference fat image projection are made have the same power spectrum as that of the complete water image projection and the complete fat image projection, which improves the accuracy of the correlation and further enhances the accuracy rate of making a distinction in the water-fat image obtained using the three-point Dixon method.

DESCRIPTION OF THE PREFERRED EMBODIMENTS

In the embodiments of the present invention, three echoes without phase encoding are first used as a reference scan, and a reference water image projection is obtained by calculation using the reference scan, and since the reference water image projection does not involve the phase encoding and phase anti-wrapping during its calculation, no image shift will appear, i.e. what corresponds to the reference water image projection would certainly be an image projection of water, and what corresponds to the reference fat image projection would certainly be an image projection of fat. Then, a complete water-fat image projection is obtained according to the water-fat image calculated by using the three-point Dixon method, and then the correlation between the reference water-fat image projection and the complete water-fat image projection is calculated, and the type of the complete water/fat image projection is determined according to the size of the correlated value, and in turn the type of the water/fat image calculated by using the three-point Dixon method is determined, so as to solve the problem of image shift.

Figure 2:
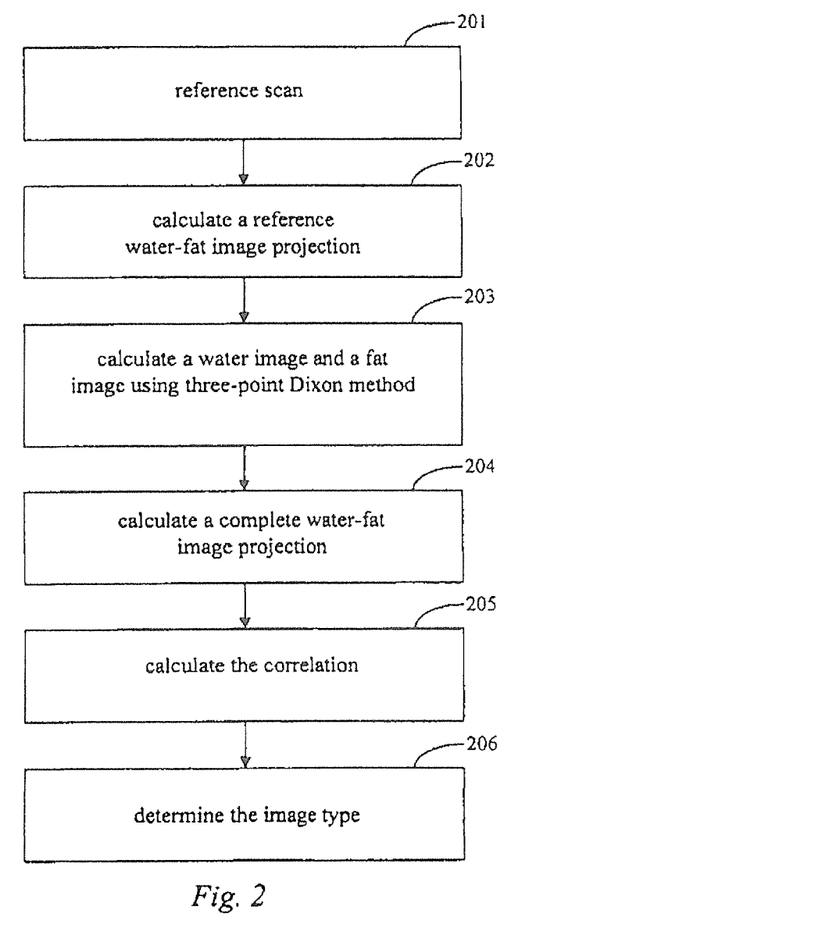
FIG. 2 is a schematic diagram of the exemplary flow of a method for making a distinction in a magnetic resonance imaging water-fat image in the embodiments of the present invention.

FIG. 2 is a schematic diagram of the exemplary flow of a method for making a distinction in a magnetic resonance imaging water-fat image in the embodiments of the present invention, and as shown in FIG. 2 the method comprises the steps as follows:

Step 201: three echoes without phase encoding are acquired as a reference scan, with said three echoes including two out-of-phase echoes and one in-phase echo, or said three echoes including two in-phase echoes and one out-of-phase echo.

In this step, the three echoes without the phase encoding refer to three echoes which are not modulated by using the phase encoding gradient applied in the phase encoding direction. Also, the three echoes can be acquired on the basis of various sequences and can have different acquisition orders, and taking the situation that the three echoes include the two out-of-phase echoes and the one in-phase echo as an example, then the three echoes can be certain three echoes which are read out according to the method shown in FIG. 1 and can also be certain three echoes which are read out by using the three-point Dixon method which is based on other sequences, such as echo sequence (SE) or gradient echo sequence (GRE), and the three echoes can be three echoes which are successively acquired according to the order of out phase-in phase-out phase as shown in FIG. 1 and can also be echoes as follows: an in-phase echo is first acquired and then two out-of-phase echoes are acquired, and can also be echoes as follows: two out-of-phase echoes are first acquired and then an in-phase echo is acquired. In this embodiment, it is assumed that the acquired three echoes without the phase encoding are echoes 1, 2, and 3 in FIG. 1. Of course, during its practical application, the three echoes without the phase encoding can also be three echoes at other locations.

As to the situation that the three echoes include the two in-phase echoes and the one out-of-phase echo, the acquisition method thereof is similar to the method described above. In the same way, they can be acquired on the basis of various sequences and can also have different acquisition orders, for example, the three echoes can be three echoes which are successively acquired according to the order of in phase-out phase-in phase, and can also be echoes as follows: an out-of-phase echo is first acquired and then two in-phase echoes are acquired, and can also be echoes as follows: two in-phase echoes are first acquired and then an out-of-phase echo is acquired.

Step 202: a reference water image projection and a reference fat image projection in the phase encoding direction are calculated using said reference scan, so as to obtain a reference water-fat image projection.

In this step, as to the situation that the three echoes include the two out-of-phase echoes and the one in-phase echo, the phase difference between two out phases can be calculated first by using two out-of-phase echoes, and then the reference water image projection and the reference fat image projection are calculated in the phase encoding direction by using the obtained phase difference.

During its practical implementation, the calculation can be carried out according to the situation of the chemical shift in the phase of water and fat in the three echoes, for example, if the chemical shift in the phase of water and fat in the two out-of-phase echoes and the one in-phase echo is $(-\pi,0,\pi)$, then the reference water-fat image projection can be calculated according to the following equation (1).

$$\Delta\phi = {ang(I3*conj(I1))}/2$$

$$w_{pr} = I2 + 0.5 \cdot (I3 \cdot e^{-j \cdot \Delta\phi} + I1 \cdot e^{j \cdot \Delta\phi})$$

$$f_{pr} = I2 - 0.5 \cdot (I3 \cdot e^{-j \cdot \Delta\phi} + I1 \cdot e^{j \cdot \Delta\phi}) \quad (1)$$

As another example: if the chemical shift in the phase of water and fat in the two out-of-phase echoes and the one in-phase echo is $(-3\pi,0,\pi)$ then the reference water-fat image projection can be calculated according to the following equation (2):

$$\Delta\phi = {ang(I3*conj(I1))}/4$$

$$w_{pr} = I2 + 0.5 \cdot (I3 \cdot e^{-j \cdot \Delta\phi} + I1 \cdot e^{j \cdot 3 \cdot \Delta\phi})$$

$$f_{pr} = I2 - 0.5 \cdot (I3 \cdot e^{-j \cdot \Delta\phi} + I1 \cdot e^{j \cdot 3 \cdot \Delta\phi}) \quad (2)$$

in which I1 and I3 are two out-of-phase echoes, I2 is one in-phase echo, if the three echoes without the phase encoding acquired in step 201 are echoes 1, 2 and 3 in FIG. 1, then I1, I2 and I3 are echoes 1, 2 and 3 respectively; ang( ) is a phase acquisition function, $\Delta\phi$ is the phase difference between two out phases; conj( ) is a conjugate function; $w_{pr}$ and $f_{pr}$ respectively are the reference water image projection and the reference fat image projection obtained by calculation directly using $\Delta\phi$ to carry out a phase correction.

In the above process, the phase correction is directly carried out by using $\Delta\phi$ when carrying out the phase correction and it does not need to first carry out the anti-wrapping processing thereon and then carry out the phase correction, and therefore, no image shift problem will occur, i.e. the reference water image projection will certainly be a reference image projection corresponding to water and will not be a reference image projection corresponding to fat, and vice versa.

As to the situation that the three echoes include the two in-phase echoes and the one out-of-phase echo, the calculation method thereof is similar to the method described above. In the same way, the phase difference between two in phases can be calculated first by using the two in-phase echoes, and then the reference water image projection and the reference fat image projection are calculated in the phase encoding direction by using the obtained phase difference.

During its practical implementation, the calculation can also be carried out according to the situation of the chemical shift in the phase of water and fat in the three echoes, for example, if the chemical shift in the phase of water and fat in the two in-phase echoes and the one out-of-phase echo is $(0,\pi,2\pi)$, then the reference water-fat image projection can be calculated according to the following equation (3).

$$\Delta\phi = {ang(l3*conj(l1))}/2$$

$$w_{pr} = 0.5 \cdot (l3 \cdot e^{-j \cdot 2 \cdot \Delta\phi} + l1) + l2 \cdot e^{-j \cdot \Delta\phi}$$

$$f_{pr} = 0.5 \cdot (l3 \cdot e^{-j \cdot 2 \cdot \Delta\phi} + l1) - l2 \cdot e^{-j \cdot \Delta\phi} \qquad (3)$$

As another example, if the chemical shift in the phase of water and fat in the two in-phase echoes and the one out-of-phase echo is $(0,\pi,4\pi)$, then the reference water-fat image projection can be calculated according to the following equation (4):

$$\Delta\phi = {ang(l3*conj(l1))}/4$$

$$w_{pr} = 0.5 \cdot (l3 \cdot e^{-j \cdot 4 \cdot \Delta\phi} + l1) + l2 \cdot e^{-j \cdot \Delta\phi}$$

$$f_{pr} = 0.5 \cdot (l3 \cdot e^{-j \cdot 4 \cdot \Delta\phi} + l1) - l2 \cdot e^{-j \cdot \Delta\phi} \qquad (4)$$

in which l1 and l3 are two in-phase echoes, l2 is one out-of-phase echo; ang( ) is a phase acquisition function, $\Delta\phi$ is the phase difference between two in phases; conj( ) is a conjugate function, $w_{pr}$ and $f_{pr}$ respectively are the reference water image projection and the reference fat image projection obtained by calculation directly using $\Delta\phi$ to carry out the phase correction.

Likewise, in the above process, the phase correction is also directly carried out by using $\Delta\phi$ when carrying out the phase correction and it does not need to first carry out the anti-wrapping processing thereon and then carry out the phase correction, and therefore, no image shift problem will occur, i.e. the reference water image projection will certainly be a reference image projection corresponding to water and will not be a reference image projection corresponding to fat, and vice versa.

During its practical application, other calculation methods can also be used, as long as they are capable of calculating the reference water image projection and reference fat image projection in the phase encoding direction by using said reference scan, which will not be listed here one by one.

Step 203: a water image and a fat image are obtained by calculation using the three-point Dixon method.

In this step, the currently available and various newly added three-point Dixon method can be used.

For example, the method for water-fat separation image reconstruction disclosed in Chinese patent application no. 200510008973.0, the inventors of which are Wang Min-jian and Weng De-he, can be used, and the method for implementing water-fat separation disclosed in Chinese patent application no. 200910119608.5, the inventors of which are Wu Dong-mei and Wang Zhen-kui, can also be used. Furthermore, the three-point Dixon method in which two in-phase images and one out-of-phase image are used to carry out water-fat image calculation can also be used, which will not be listed here one by one.

Step 204: a water image projection and a fat image projection in the phase encoding direction are calculated by using said water image and fat image. In order to differentiate from the reference water image projection and the reference fat image projection in step 202, here they are referred to as a complete water image projection and a complete fat image projection respectively, thereby obtaining a complete water-fat image projection.

In this step, there can be various methods for calculating the complete water image projection and the complete fat image projection in the phase encoding direction, and a calculation method among them is listed as the following equation (5):

$$w_{pc} = \sum_{i=1}^{n} w_i, \quad f_{pc} = \sum_{i=1}^{n} f_i \qquad (5)$$

in which $w_{pc}$ and $f_{pc}$ are the complete water image projection and the complete fat image projection respectively, $w_i$ and $f_i$ are voxel point data along the phase encoding direction respectively, and n is the resolution in the phase encoding direction.

During its practical implementation, other calculation methods except equation (5) can also be used, as long as the complete water image projection and the complete fat image projection in the phase encoding direction can be obtained by calculation using said water image and said fat image, which will not be listed here one by one.

Step 205: the correlation between the reference water-fat image projection and the complete water-fat image projection is calculated, so as to obtain at least two correlated values.

In this step, when the correlation between the reference water-fat image projection and the complete water-fat image projection is calculated, there can be various combinations. For example, the correlation between the reference water image projection and the complete water image projection, the correlation between the reference water image projection and the complete fat image projection, the correlation between the reference fat image projection and the complete water image projection, and the correlation between the reference fat image projection and the complete fat image projection can be calculated, so as to obtain four correlated values.

Alternatively, it is possible for only two correlated values therein which are comparable to be calculated. For example, it is possible for only the correlation between the reference water image projection and the complete water image projection and the correlation between the reference water image projection and the complete fat image projection to be calculated, so as to obtain two correlated values. In this case, it is possible for only the reference water image projection to be calculated in step 202, i.e. it is possible for the reference fat image projection not to be calculated, and in this case, it is possible for the reference water-fat image projection to include only the reference water image projection. Of course, the reference fat image projection can also be calculated.

As another example, it is possible for only the correlation between the reference fat image projection and the complete water image projection and the correlation between the reference fat image projection and the complete fat image projection to be calculated, so as to obtain two correlated values. In this case, it is possible for only the reference fat image projection to be calculated in step 202, i.e. it is possible for the reference water image projection not to be calculated, and in this case, the reference water-fat image projection can include only the reference fat image projection. Of course, the reference water image projection can also be calculated.

As still another example, it is also possible for only the correlation between the reference water image projection and the complete water image projection and the correlation between the reference water fat projection and the complete fat image projection to be calculated, so as to obtain two correlated values. In this case, it is possible for only the complete water image projection to be calculated in step 204, i.e. it is possible for the complete fat image projection not to be calculated, and in this case, the complete water-fat image projection can include only the complete water image projection. Of course, the complete fat image projection can also be calculated.

As yet another example, it is possible for only the correlation between the reference water image projection and the complete fat image projection and the correlation between the reference fat image projection and the complete fat image projection to be calculated, so as to obtain two correlated values. In this case, it is possible for only the complete fat image projection to be calculated in step 204, i.e. it is possible for the complete water image projection not to be calculated, and in this case, the complete water-fat image projection can include only the complete fat image projection. Of course, the complete water image projection can also be calculated.

In this step, as to $w_{pr}$ and $f_{pr}$ which represent the reference water image projection and the reference fat image projection respectively and $w_{pc}$ and $f_{pc}$ which represent the complete water image projection and the complete fat image projection respectively, the correlation between $w_{pr}$ and $w_{pc}$, the correlation between $w_{pr}$ and $f_{pc}$, the correlation between $f_{pr}$ and $w_{pc}$, and the correlation between $f_{pr}$ and $f_{pc}$ can be calculated, so as to obtain four correlated values in total. Alternatively, it is possible for only two correlated values therein which are comparable to be calculated, for example, it is possible for only the correlation between $w_{pr}$ and $w_{pc}$ and the correlation between $w_{pr}$ and $f_{pc}$; or the correlation between $f_{pr}$ and $w_{pc}$ and the correlation between $f_{pr}$ and $f_{pc}$; or the correlation between $w_{pr}$ and $w_{pc}$ and the correlation between $f_{pr}$ and $w_{pc}$; or the correlation between $w_{pr}$ and $f_{pc}$ and the correlation between $f_{pr}$ and $f_{pc}$ to be calculated.

During its practical implementation, the above correlation can be calculated by using equation (6):

$$C_{rc}=\max(\mathrm{FT}(\mathrm{FT}(P_r)\cdot\mathrm{conj}(\mathrm{FT}(P_c)))) \quad (6)$$

in which, $C_{rc}$ is a correlated value, $P_r$ is $w_{pr}$ or $f_{pr}$, $P_c$ is $w_{pc}$ or $f_{pc}$, FT( ) is a Fourier transform function, conj( ) is a conjugate function; and max( ) is maximum function.

During its particular application, since the reference water-fat image projection obtained in step 202 and the complete water-fat image projection obtained in step 204 generally have different power spectrum amplitudes, in order to acquire the same power spectrum as that of the complete water-fat image projection obtained in step 204, before the correlation calculation, the reference water-fat image projection can first be normalized, and then the above correlation calculation is carried out by using the normalized reference water-fat image projection. Of course, it is possible for the normalization not to be carried out.

During its practical implementation, other calculation methods except equation (6) can also be used, for example, the correlation is calculated by using the following equation (7):

$$C_{rc}=\mathrm{sum}(\mathrm{abs}(P_r-P_c)) \quad (7)$$

in which, $C_{rc}$ is a correlated value, $P_r$ is $w_{pr}$ or $f_{pr}$, $P_c$ is $w_{pc}$ or $f_{pc}$, sum is a summing operator, and abs is an absolute value operator.

In addition, other calculation methods can also be used, as long as they can obtain by calculation the correlation between the reference water image projection and complete water image projection and complete fat image projection and the correlation between reference fat image projection and complete water image projection and complete fat image projection, which will not be listed here one by one.

Step 206: the maximum correlated value from the correlated values obtained by calculation is acquired, and the type of said complete image projection corresponding to said maximum correlated value is determined as the type of a reference image projection corresponding to the maximum correlated value, and the type of an image obtained by calculation using the three-point Dixon method is determined according to the type of said complete image projection, i.e. the image type calculated in step 203.

By way of the method described above, whether shift occurs between water and fat images calculated by using the three-point Dixon method in step 203 can be verified.

During its practical implementation, there is no absolute sequential order between steps 201-202 and steps 203-204, i.e. steps 203-204 can be performed first and then steps 201-202 are performed, or steps 201-202 and steps 203-204 can be performed in parallel or alternately.

The foregoing has described the method for making a distinction in a magnetic resonance imaging water-fat image in the embodiments of the present invention in detail, and hereinafter, the apparatus for making a distinction in a magnetic resonance imaging water-fat image will be described in detail.

Figure 3:
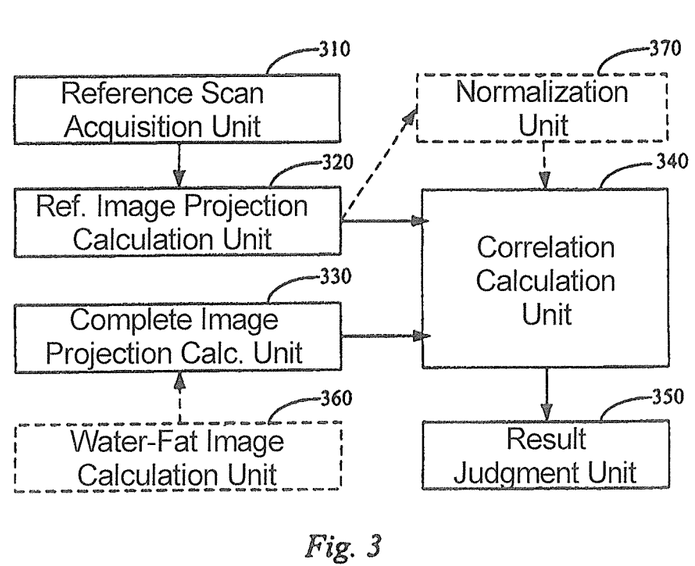
FIG. 3 is a schematic diagram of the exemplary structure of an apparatus for making a distinction in a magnetic resonance imaging water-fat image in the embodiments of the present invention.

FIG. 3 is a schematic diagram of the exemplary structure of an apparatus for making a distinction in a magnetic resonance imaging water-fat image in the embodiments of the present invention, and as shown in FIG. 3, the apparatus includes: a reference scan acquisition unit 310, a reference image projection calculation unit 320, a complete image projection calculation unit 330, a correlation calculation unit 340, and a result judgment unit 350.

In this case, the reference scan acquisition unit 310 is used for acquiring three echoes without phase encoding as a reference scan. Here, said three echoes include two out-of-phase echoes and one in-phase echo, or said three echoes include two in-phase echoes and one out-of-phase echo. During its practical implementation, the particular operation process of reference scan acquisition unit 310 is identical to the particular operation process described in step 201.

The reference image projection calculation unit 320 is used for calculating a reference water image projection and a reference fat image projection in the phase encoding direction to obtain a reference water-fat image projection by using said reference scan acquired by the reference scan acquisition unit 310. During its practical implementation, the particular operation process of reference image projection calculation unit 320 is identical to the particular operation process described in step 202.

The complete image projection calculation unit 330 is used for calculating a complete water image projection and a complete fat image projection in the phase encoding direction to obtain a complete water-fat image projection according to a water image and a fat image obtained by calculation using a three-point Dixon method. During its practical implementation, the particular operation process of the complete image projection calculation unit 330 is identical to the particular operation process described in step 204.

Here, the water image and fat image obtained by calculation using the three-point Dixon method can be obtained by calculation using an apparatus other than the apparatus in this embodiment, then, the apparatus in this embodiment does not comprise a water-fat image calculation unit; alternatively, they can be obtained by calculation using the apparatus in this embodiment, then, the apparatus in this embodiment further comprises a water-fat image calculation unit 360 (as shown by the dashed line portion in FIG. 3) for obtaining a water image and a fat image using the three-point Dixon method to carry out calculation and providing said water image and fat image to said complete image projection calculation unit 330 to carry out the calculation of complete water-fat image projection.

The correlation calculation unit 340 is used for calculating the correlation between the reference water-fat image projection and complete water-fat image projection using the reference water-fat image projection obtained by said reference image projection calculation unit 320 and the complete water-fat image projection obtained by said complete image projection calculation unit 330 to obtain at least two correlated values. During its practical implementation, the particular operation process of the correlation calculation unit 340 is identical to the particular operation process described in step 205. That is, there also exists the correlation calculation of various combinations described in step 205. Accordingly, when it only needs to calculate two correlated values which are comparable, it is possible for the reference image projection calculation unit 320 or the complete image projection calculation unit 330 to calculate only one image projection required by correlation calculation; then, the reference water-fat image projection or complete water-fat image projection can include only one corresponding image projection. Of course, it is also possible to calculate all of them.

The result judgment unit 350 is used for acquiring the maximum correlated value from the correlated values obtained by the correlation calculation unit 340, determining the type of the complete image projection corresponding to said maximum correlated value as the type of a reference image projection corresponding to the maximum correlated value, and determining the type of an image obtained by calculation using the three-point Dixon method according to the type of said complete image projection.

During its practical implementation, if it is intended to enable the reference water-fat image projection and complete water-fat image projection to have the same power spectrum, before correlation calculation, the reference water-fat image projection can be normalized first, and then the above correlation calculation is carried out by using the normalized reference water-fat image projection. Then, the apparatus in this embodiment can further comprise a normalization unit 370 (as shown by the dashed line portion in FIG. 3) for normalizing the reference water-fat image projection obtained by said reference image projection calculation unit 320. Accordingly, the correlation calculation unit 340 is used for calculating the correlation between the reference water-fat image projection and complete water-fat image projection using the reference water-fat image projection normalized by said normalization unit 370 and the complete water-fat image projection obtained by said complete image projection calculation unit 330 to obtain at least two correlated values. Of course, it is possible for the normalization not to be carried out, then, the apparatus in this embodiment does not need to comprise the normalization unit 370.

Figure 4:
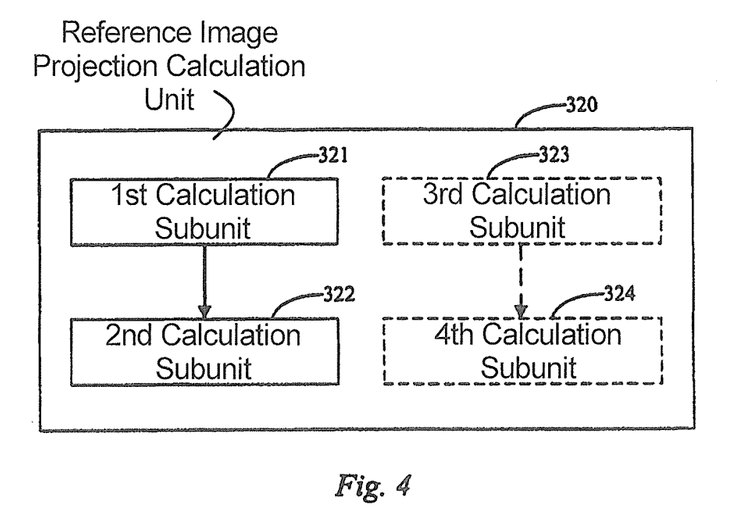
FIG. 4 is a schematic structural diagram of a reference image projection calculation unit in the embodiments of the present invention.

During its practical implementation, based on different calculation methods, the reference image projection calculation unit 320 can have different internal structures, and FIG. 4 shows an internal structure of the reference image projection calculation unit 320. As shown by the solid line portion in FIG. 4, the reference image projection calculation unit 320 can include:
  a first calculation subunit 321 for calculating the phase difference between two out phases by using two out-of-phase echoes; and
  a second calculation subunit 322 for calculating the reference water image projection and/or reference fat image projection in the phase encoding direction by using the phase difference obtained by said first calculation subunit 321.

Alternatively, as shown by the dashed line portion in FIG. 4, the reference image projection calculation unit 320 can also includes:
  a third calculation subunit 323 for calculating the phase difference between two in phases by using two in-phase echoes; and
  a fourth calculation subunit 324 for calculating the reference water image projection and/or reference fat image projection in the phase encoding direction by using the phase difference obtained by said third calculation subunit 323.

Again alternatively, the reference image projection calculation unit 320 can also simultaneously include the above four calculation subunits, and during particular calculations, the reference image projection calculation unit 320 can select therefrom according to the type of reference scanning, i.e. a selection unit judges the type of reference scanning; if the reference scan includes two out-of-phase echoes and one in-phase echo, then the reference image projection calculation unit 320 selects to use the first calculation subunit 321 and second calculation subunit 322; and if the reference scan includes two in-phase echoes and one out-of-phase echo, then the reference image projection calculation unit 320 selects to use the third calculation subunit 323 and fourth calculation subunit 324.

Figure 5:
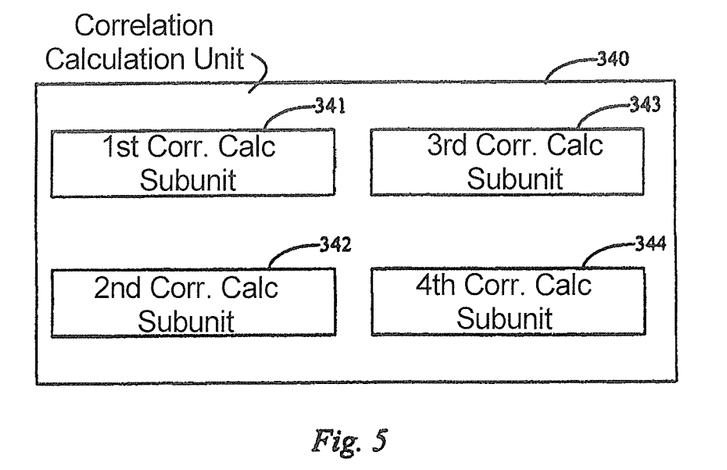
FIG. 5 is a schematic structural diagram of a correlation calculation unit in the embodiments of the present invention.

During its practical implementation, based on different correlation combinations, the correlation calculation unit 340 can also have different internal structure, and FIG. 5 shows a schematic diagram of an internal structure of the correlation calculation unit 340. As shown in FIG. 5, the correlation calculation unit 340 includes:
  a first correlation calculation subunit 341 for calculating the correlation between the reference water image projection and complete water image projection;
  a second correlation calculation subunit 342 for calculating the correlation between the reference water image projection and complete fat image projection;
  a third correlation calculation subunit 343 for calculating the correlation between the reference fat image projection and complete water image projection; and
  a fourth correlation calculation subunit 344 for calculating the correlation between the reference fat image projection and complete fat image projection.

In addition, based on other correlation combinations, the correlation calculation unit 340 can also include only the above first correlation calculation subunit 341 and second correlation calculation subunit 342; or only the above third correlation calculation subunit 343 and fourth correlation calculation subunit 344; or only the above first correlation calculation subunit 341 and third correlation calculation subunit 343; or only the above second correlation calculation subunit 342 and fourth correlation calculation subunit 344.

The foregoing describes the apparatus for making a distinction in a magnetic resonance imaging water-fat image in an embodiment of the present invention in detail. During its practical implementation, the apparatus for making a distinction in a magnetic resonance imaging water-fat image can also have internal structures in other forms, for example, the above function units can be recombined or further refined. Furthermore, each function unit can be located in different entities and can also all located in the same entity, which can be configured as required.

Figure 6:
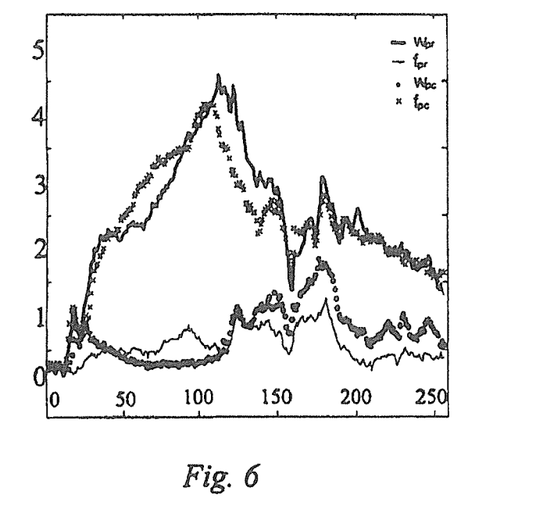
FIG. 6 shows a reference water-fat image projection and a complete water-fat image projection obtained by using the technical solution of the present invention on 0.35 T magnetic resonance imaging equipment.

The inventors of the present application used one set of 0.35 T magnetic resonance imaging equipment to carry out head imaging with water-fat separation. The parameters used included: field of view (FOV)=24×24 cm, echo time/repeat time (TE/TR)=34/695 ms, and matrix=256×256. FIG. 6 is a reference water image projection, reference fat image projection, complete water image projection and complete fat image projection obtained by the inventors of the present application using the method of the present invention. The horizontal coordinate in the figure is pixel point and the vertical coordinate is projection value. It can be seen from FIG. 6 that $w_{pr}$ and $f_{pc}$ have relatively good correlation, and $f_{pr}$ and $w_{pc}$ have relatively good correlation, therefore, the fat image and water image can be determined.

Figure 7:
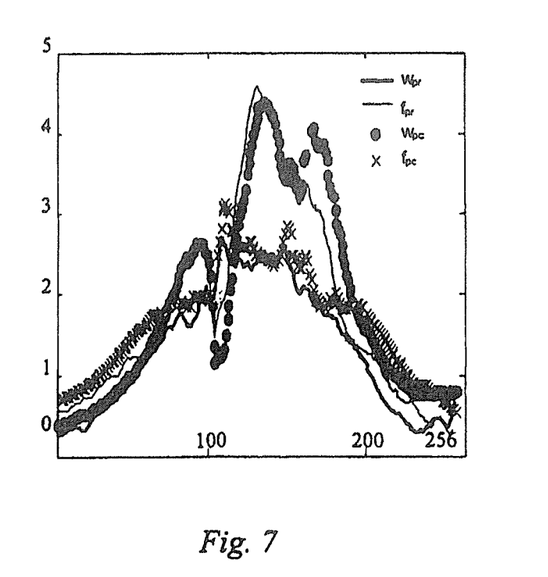
FIG. 7 shows a reference water-fat image projection and a complete water-fat image projection obtained by using the technical solution of the present invention on 1.5 T magnetic resonance imaging equipment.

The inventors of the present application also used one set of 1.5 T magnetic resonance imaging equipment to carry out knee imaging with water-fat separation. The parameters used included: field of view (FOV)=26.3×35 cm, echo time/repeat time (TE/TR)=13/3500 ms, and matrix=231×256. FIG. 7 is a reference water image projection, reference fat image projection, complete water image projection and complete fat image projection obtained by the inventors of the present application using the method of the present invention. The horizontal coordinate in the figure is pixel point and the vertical coordinate is projection value. It can be seen from FIG. 7 that $w_{pr}$ and $f_{pc}$ have relatively good correlation and $f_{pr}$ and $w_{pc}$ have relatively good correlation, therefore, the fat image and water image can be determined.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for making a distinction in a magnetic resonance imaging water-fat image, comprising:
   acquiring three echoes without phase encoding as a reference scan;
   calculating at least one of a reference water image projection and a reference fat image projection in the phase encoding direction using said reference scan, so as to obtain a reference water-fat image projection;
   calculating at least one of a complete water image projection and a complete fat image projection in the phase encoding direction according to a water image and a fat image obtained by calculation using a three-point Dixon method, so as to obtain a complete water-fat image projection;
   calculating a correlation between the reference water-fat image projection and the complete water-fat image projection, so as to obtain at least two correlated values; and
   acquiring a maximum correlated value from the correlated values obtained by calculation, and determining a type of the image calculated by using the three-point Dixon method.

2. The method as claimed in claim 1, comprising normalizing the reference water-fat image projection before calculating the correlation.

3. The method as claimed in claim 1 wherein that calculating the correlation comprises:
   calculating at least two of a correlation between the reference water image projection and the complete water image projection, a correlation between the reference water image projection and the complete fat image projection, a correlation between the reference fat image projection and the complete water image projection, and a correlation between the reference fat image projection and the complete fat image projection.

4. The method as claimed in claim 3, comprising:
   calculating the correlation according to one of $$C_{rc} = \max(FT(FT(P_r) \cdot \operatorname{conj}(FT(P_c))))$$

or $$C_{rc} = \operatorname{sum}(\operatorname{abs}(P_r - P_c))$$

wherein $C_{rc}$ is a correlated value, $P_r$ is $w_{pr}$ or $f_{pr}$, $P_c$ is $w_{pc}$ or $f_{pc}$, FT( ) is a Fourier transform function, conj( ) is a conjugate function, max( ) is a maximum function, sum is a summing operator, abs is an absolute operator; and wherein $w_{pr}$ and $f_{pr}$ are reference water image projection and reference fat image projection respectively, and $w_{pc}$ and $f_{pc}$ are complete water image projection and complete fat image projection respectively.

5. The method as claimed in claim 1, wherein said three echoes include two out-of-phase echoes and one in-phase echo, and calculating a phase difference between two out-of-phases by using two out-of-phase echoes, and calculating said at least one of the reference water image projection and reference fat image projection in the phase encoding direction using the obtained phase difference;
   or,
   said three echoes include two in-phase echoes and one out-of-phase echo; and calculating a phase difference between two in-phases using two in-phase echoes, and calculating said at least one of the reference water image projection and reference fat image projection in the phase encoding direction using the obtained phase difference.

6. The method as claimed in claim 5, comprising:
   when the chemical shift phase of water and fat in the two out-of-phase echoes and the one in-phase echo is $(-\pi, 0, \pi)$, calculating the reference water image projection and reference fat image projection according to $$\Delta\phi = {}^{ang(l3 * conj(l1))}/2$$

$$w_{pr} = l2 + 0.5 \cdot (l3 \cdot e^{-j \cdot \Delta\phi} + l1 \cdot e^{j \cdot \Delta\phi})$$

$$f_{pr} = l2 - 0.5 \cdot (l3 \cdot e^{-j \cdot \Delta\phi} + l1 \cdot e^{j \cdot \Delta\phi})$$

and
   when the chemical shift phase of water and fat in the two out-of-phase echoes and the one in-phase echo is $(-3\pi, 0, \pi)$, calculating the reference water image projection and reference fat image projection according to $$\Delta\phi = {}^{ang(l3 * conj(l1))}/4$$

$$w_{pr} = l2 + 0.5 \cdot (l3 \cdot e^{-j \cdot \Delta\phi} + l1 \cdot e^{j \cdot 3 \cdot \Delta\phi})$$

$$f_{pr} = l2 - 0.5 \cdot (l3 \cdot e^{-j \cdot \Delta\phi} + l1 \cdot e^{j \cdot 3 \cdot \Delta\phi})$$

wherein l1 and l3 are the two out-of-phase echoes, l2 is the one in-phase echo; ang( ) is a phase acquisition function, $\Delta\phi$ is the phase difference between two out phases; conj( ) is a conjugate function, and $w_{pr}$ and $f_{pr}$ are reference water image projection and reference fat image projection respectively obtained by calculation directly using $\Delta\phi$ to carry out a phase correction.

7. The method as claimed in claim 5, wherein
   when the chemical shift phase of water and fat in the two in-phase echoes and the one out-of-phase echo is $(0, \pi, 2\pi)$, calculating the reference water image projection and reference fat image projection according to $$\Delta\phi = {}^{ang(l3*conj(l1))}/2$$

$$w_{pr}=0.5\cdot(l3\cdot e^{-j\cdot 2\cdot\Delta\phi}+l1)+l2\cdot e^{-j\cdot\Delta\phi}$$

$$f_{pr}=0.5\cdot(l3\cdot e^{-j\cdot 2\cdot\Delta\phi}+l1)-l2\cdot e^{-j\cdot\Delta\phi}$$

and when the chemical shift phase of water and fat in the two in-phase echoes and the one out-of-phase echo is $(0,\pi,4\pi)$, calculating the reference water image projection and reference fat image projection according to $$\Delta\phi = {}^{ang(l3*conj(l1))}/4$$

$$w_{pr}=0.5\cdot(l3\cdot e^{-j\cdot 4\cdot\Delta\phi}+l1)+l2\cdot e^{-j\cdot\Delta\phi}$$

$$f_{pr}=0.5\cdot(l3\cdot e^{-j\cdot 4\cdot\Delta\phi}+l1)-l2\cdot e^{-j\cdot\Delta\phi}$$

wherein l1 and l3 are the two in-phase echoes, l2 is the one out-of-phase echo; ang( ) is a phase acquisition function, $\Delta\phi$ is the phase difference between two in phases; is a conjugate function; and $w_{pr}$ and $f_{pr}$ are reference water image projection and reference fat image projection respectively obtained by calculation directly using $\Delta\phi$ to carry out a phase correction.

8. An apparatus for making a distinction in a magnetic resonance imaging water-fat image, comprising:
a reference scan acquisition unit configured to acquire three echoes without phase encoding as a reference scan;
a reference image projection calculation unit configured to calculate at least one of a reference water image projection and a reference fat image projection in the phase encoding direction using said reference scan, so as to obtain a reference water-fat image projection;
a complete image projection calculation unit configured to calculate at least one of a complete water image projection and a complete fat image projection in the phase encoding direction according to a water image and a fat image obtained by calculation using a three-point Dixon method, so as to obtain a complete water-fat image projection;
a correlation calculation unit configured to calculate a correlation between the reference water-fat image projection and the complete water-fat image projection, so as to obtain at least two correlated values; and
a result judgment unit configured to acquire a maximum correlated value from said correlated values, and determine a type of the image calculated by using the three-point Dixon method.

9. The apparatus as claimed in claim 8, comprising:
a normalization unit configured to normalize the reference water-fat image projection obtained by said reference image projection calculation unit and provide the normalized reference water-fat image projection to said correlation calculation unit.

10. The apparatus as claimed in claim 8, comprising:
a water-fat image calculation unit configured to provide the water image and the fat image to said complete image projection calculation unit using said water image and said fat image obtained by calculation using a three-point Dixon method.

11. The apparatus as claimed in claim 8, wherein said reference image projection calculation unit comprises:
a first calculation subunit configured to calculate a phase difference between two out phases using two out-of-phase echoes;
a second calculation subunit configured to calculate said at least one of the reference water image projection and the reference fat image projection in the phase encoding direction using the phase difference obtained by said first calculation subunit;
and,
a third calculation subunit configured to calculate a phase difference between two in phases using two in-phase echoes; and
a fourth calculation subunit configured to calculate said at least one of the reference water image projection and the reference fat image projection in the phase encoding direction using the phase difference obtained by said third calculation subunit.

12. The apparatus as claimed in claim 8, wherein said correlation calculation unit comprises at least two of; a first correlation calculation subunit, a second correlation calculation subunit, a third correlation calculation subunit, and a fourth correlation calculation subunit;
wherein said first correlation calculation subunit is configured to calculate a correlation between the reference water image projection and the complete water image projection;
said second correlation calculation subunit is configured to calculate a correlation between the reference water image projection and the complete fat image projection;
said third correlation calculation subunit is configured to calculate a correlation between the reference fat image projection and the complete water image projection; and
said fourth correlation calculation subunit is configured to calculate a correlation between the reference fat image projection and the complete fat image projection.

* * * * *